United States Patent [19]

Toukan et al.

[11] 4,126,633

[45] Nov. 21, 1978

[54] FLUORINATED ALIPHATIC SULFIDES

[75] Inventors: Sameeh S. Toukan, Phoenixville; Murray Hauptschein, Glenside, both of Pa.

[73] Assignee: Pennwalt Corporation, Philadelphia, Pa.

[21] Appl. No.: 721,242

[22] Filed: Sep. 8, 1976

Related U.S. Application Data

[63] Continuation of Ser. No. 396,648, Sep. 12, 1973, abandoned, which is a continuation-in-part of Ser. No. 171,325, Aug. 21, 1971, abandoned.

[51] Int. Cl.² ............................................ C07C 149/16
[52] U.S. Cl. ........................ 260/501.12; 260/583 EE; 252/307; 252/357
[58] Field of Search ...................... 260/501.12, 501.13

[56] References Cited

U.S. PATENT DOCUMENTS

| 3,171,861 | 3/1965 | Ahlbrecht | 260/567.6 M |
| 3,172,910 | 3/1965 | Brace | 260/567.6 M |
| 3,678,110 | 7/1972 | Boothe et al. | 260/567.6 M |
| 3,721,706 | 3/1973 | Hoffmann et al. | 260/501.12 |

FOREIGN PATENT DOCUMENTS

| 758,156 | 7/1954 | United Kingdom | 260/567.6 M |
| 773,326 | 4/1955 | United Kingdom | 260/567.6 M |

Primary Examiner—Nicky Chan

[57] ABSTRACT

Fluorinated aliphatic sulfides, represented by $R_f(CH_2)_nS(CH_2)_mQ$ wherein $R_f$ is fluoroalkyl, $n$ is 2 or 3, $m$ is an integer from 2 to 4, Q is $-N(R)_2$ or $-N^{\oplus}(R)_2CH_2COOH\ X^{\ominus}$ where X is Cl or Br, and R is an alkyl group of 1 to 4 carbon atoms, are particularly effective amphoteric surface-tension depressants or intermediates therefor.

6 Claims, No Drawings

FLUORINATED ALIPHATIC SULFIDES

This is a continuation of application Ser. No. 396,648, filed Sept. 12, 1973 now abandoned; which in turn is a continuation-in-part of Ser. No. 171,325, filed Aug. 21, 1971, now abandoned.

This invention concerns novel fluorinated aliphatic sulfides. More particularly, this invention is directed to fluorinated alkyl sulfides represented by $R_f(CH_2)_nS(CH_2)_mQ$ where $R_f$ is a radical selected from the group consisting of perfluoroalkyl, perfluoroisoalkoxyalkyl, and perfluoromonochloroalkyl radicals having from 5 to 13 carbon atoms, preferably from 7 to 11 carbon atoms, $n$ is 2 or 3, $m$ is an integer from 2 to 3, and Q is $-N(R)_2$ or $-N^{\oplus}(R)_2 CH_2COOH\ X^{\ominus}$ where X is Cl or Br, and R is an alkyl group of 1 to 4 carbon atoms. Particularly preferred are the compounds wherein $n$ is 2, $m$ is 2, X is Cl, and R is methyl.

A perfluoroalkyl radical is defined as one containing only carbon and fluorine; a perfluoroisoalkoxyalkyl radical contains only carbon, fluorine, and an oxygen in an ether linkage; a perfluoromonochloroalkyl radical is one which contains only fluorine, chlorine and carbon; any of the foregoing radicals may be straight chain or branched chain. The preferred $R_f$ radical is perfluoroalkyl. Representative $R_f$ radicals are, for example, $(CF_3)_2CF(CF_2CF_2)-$
$(CF_3)_2CF(CF_2CF_2)_3-$
$C_7F_{15}-$
$C_{11}F_{23}-$
$(CF_3)_2CFO(CF_2CF_2)-$
$CF_3)_2CFO(CF_2CF_2)_4-$
$(CF_3)(CF_2Cl)CF(CF_2CF_2)-$
$C_7ClF_{14}-$
$C_8F_{17}$
$CF_2Cl(CF_2)_{10}-$
$C_9F_{19}$
$C_{10}F_{21}$
$C_{13}F_{27}$ In one method for preparing the surfactants of this invention, a fluoroalkylalkylene halide is first reacted with a mercaptan in the presence of a basic substance, such as NaOH, to first produce the sulfide products according to the exemplary reaction:

$R_f(CH_2)_nX' + HS(CH_2)_mN(R)_2 + NaOH \rightarrow$
$R_f(CH_2)_nS(CH_2)_mN(R)_2 + NaX' + H_2O$ where X' is Br or I, and R, $R_f$, $n$, and $m$ are as defined earlier. The resulting amine derivative is then reacted with chloroacetic acid, or bromoacetic acid to give the amphoteric surfactants,

Among the basic materials that may be used in the above-described reaction to prepare the amine derivative are alkali metal hydroxides, e.g., KOH and LiOH, and preferably NaOH, and such basic substances as triethylamine, sodium methoxide, potassium tert.-butoxide, and like substances. The reaction is carried out by bringing the above-described reactants together at a temperature within the range of about 50 to about 150° C., preferably about 80° to 100° C. The reaction is normally carried out under atmospheric pressure. Reaction periods ranging from 1 to 24 hours are usually adequate, with from about 2 to 6 hours normally satisfactory. The reaction preferably is conducted with the reactants in admixture in medium comprising organic polar liquid, which shows solvency for the fluoroalkylethylene halide, for example, methanol, ethanol, n-propanol, isopropanol, n-amyl alcohol, n-hexanol, n-octanol, sec-butanol, N-butanol, isobutanol, tert-butanol, isoamyl alcohol, tert-amyl alcohol, 2-pentanol, cyclohexanol, 2-ethyl-1-hexanol and mixtures of said liquids. The weight ratio of polar solvent to fluoroalkylalkylene halide will generally be in the range of about 2:1 to about 10:1. In the more preferred embodiments the solvent is essentially anhydrous.

Other synthesis routes (e.g., those disclosed by Rondestvedt, U.S. Pat. No. 3,655,732) to these compounds will be readily apparent to one skilled in the art.

The fluorinated-alkyl sulfide amphoteric compounds of the invention are particularly effective surface-tension depressants for aqueous systems. In the following examples, which illustrate and clarify the present invention, the infrared spectrum of each synthesized product is consistent with the structure set forth.

EXAMPLE 1

Preparation of
$C_9F_{19}CH_2CH_2SCH_2CH_2N^{\oplus}(CH_3)_2CH_2COOH^{\ominus}Cl$ To a stirred solution of 4.0 g. (0.1 mole) of NaOH in 50 ml. of abs. ethanol is added 7.1 g. (0.05 mole) of 2-dimethylamino-ethylthiol hydrochloride and the mixture is heated for 10–15 minutes at about 50° C. It is then added slowly to a solution of 31.2 g. (0.05 mole) of $(CF_3)_2CF(CF_2)_6CH_2CH_2I$ in 100 ml. of tertiary amyl alcohol, and the entire mixture refluxed for 7 hours. The reddish-brown reaction mixture is filtered to remove 3.0 g. of white solid (NaCl). The filtrate is stripped of solvent under reduced pressure at 40°–50° C., and the residue thrice extracted with 150 ml. portions of hot diethyl ether leaving 6.8 g. of unextractable light-brown solid. The combined ether-extract is washed with 150 ml. of water, 150 ml. of 5% NaOH and 150 ml. of water, and then dried. Evaporation of the solvent on a steam bath leaves 18.0 g. (60% yield) of a light-reddish-brown liquid residue. Distillation under vacuum affords 46% yield of the amine $(CF_3)_2CF(CF_2)_6CH_2CH_2SCH_2CH_2N(CH_3)_2$, b.p. 94° C. (0.4 mm. Hg), $n_D^{26}$ 1.3716.

Analysis: Calcd. for $C_{15}H_{14}F_{19}NS$: C, 30.0%; H, 2.35%; N, 2.33%. Found: C, 30.7%, H, 2.56%; N, 2.57%.

A mixture of 6.0 g. (0.01 mole) of the above tertiary amine and 0.95 g. (0.01 mole) of monochloroacetic acid is heated slowly with occasional shaking in an oil bath to 125°–130° C., thereafter the heat is turned off and the reaction mixture is kept in the oil bath while the temperature slowly falls to about 30° C. There is obtained 6.9 g. of the desired surfactant as an amber-colored waxy solid, m.p. 172°–176° (dec.).

Analysis: Calcd. for $C_{17}H_{17}ClF_{19}NO_2S$: C, 29.3%; H, 2.47%; N, 2.01%. Found: C, 29.1%; H, 2.78%; N, 2.20%.

EXAMPLE 2

Preparation of
$C_7F_{15}CH_2CH_2SCH_2CH_2N^{\oplus}(CH_3)_2CH_2COOH\ Cl^{\ominus}$ Following the procedure of Example 1, the colorless liquid product $(CF_3)_2CF(CF_2)_4CH_2CH_2SCH_2CH_2N(CH_3)_2$ is prepared in 36% yield, $n_D{}^{25.5}$ 1.3717.

Analysis: Calcd. for $C_{13}H_{14}F_{15}NS$: C, 31.2%; H, 2.81%; N, 2.79% Found: C, 31.4%; H, 2.93%; N, 3.15%.

A mixture of 5.0 g. (0.01 mole) of the above amine and 0.95 g. (0.01 mole) of monochloroacetic acid is heated slowly with occasional shaking in an oil bath to 125°–130° C. The reaction mixture is kept in the oil bath after shutting off the heat until the temperature falls to about 30° C. There is obtained 5.9 g. of the desired product as an amber-colored waxy (soft) solid.

Analysis: Calcd. for $C_{15}H_{17}ClF_{15}NO_2S$: C, 30.2%; H, 2.88%; Cl, 5.95%; N, 2.35%. Found: C, 30.7%; H, 3.25%; Cl, 5.69%; N, 2.75%.

Surface tension values (in dynes/cm.) of aqueous solutions at 25° C. of the products of Examples 1 and 2 are tabulated below, along with that for the one presently available (on a commercial scale) fluorinated surfactant.

| Product | Surface Tension, dynes/cm. at Concentration of | | |
|---|---|---|---|
| | 1% | 0.1% | 0.01% |
| Example 1 | 18 | 19 | 25 |
| Example 2 | 17 | 17 | 19 |
| $C_8F_{17}SO_2\overset{\oplus}{N}H(CH_2)_3\overset{\ominus}{N}(CH_3)_2CH_2CH_2COO$ | — | 19 | 27 |

It is noteworthy that excellent performance is obtained with the surfactants of this invention, and especially with a shorter chain-length in the expensive fluorinated portion. The surfactants embodied herein also exhibit excellent performance when compared with the amphoteric surfactants disclosed in Hager and Walters application Ser. No. 145,556, filed May 20, 1971, now U.S. Pat. No. 3,759,981. Furthermore, the compounds of this invention also have the advantage of not containing hydrolyzable ester or amide linkages.

We claim:

1. A fluorinated alkyl sulfide of the structure $R_f(CH_2)_nS(CH_2)_mQ$ where $R_f$ is selected from the class consisting of perfluoroalkyl, perfluoroisoalkoxyalkyl, and perfluoromonochloroalkyl radicals having from 5 to 13 carbon atoms, Q is [—N(R)$_2$ or]—N$^{\oplus}$(R)$_2$CH$_2$COOHX$^{\ominus}$, $n$ is 2 or 3, $m$ is an integer from 2 to 4, R is an alkyl group of 1 to 4 carbon atoms, and X is Cl or Br.

2. A compound according to claim 1 wherein $R_f$ has 7 to 11 carbon atoms.

3. A compound according to claim 2 wherein $n$ is 2 and $m$ is 2.

4. A compound according to claim 3 wherein Q is $N^{\oplus}(CH_3)_2CH_2COOH\ Cl^{\ominus}$ 5. The compound

where $R_f$ is a perfluoroalkyl group of 7 to 11 carbon atoms.

6. A compound of the formula

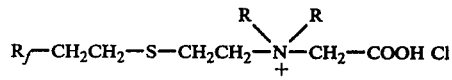

wherein $R_f$ is perfluoroalkyl of 5 to 13 carbon atoms and R is an alkyl of 1 to 4 carbon atoms.

* * * * *